United States Patent [19]

Konrad et al.

[11] 4,279,613

[45] Jul. 21, 1981

[54] METHOD AND COMPOSITION FOR HAIR COLORING

[75] Inventors: Eugen Konrad, Darmstadt, Fed. Rep. of Germany; Herbert Mager, Fribourg, Switzerland

[73] Assignee: Wella Aktiengesellschaft, Darmstadt, Fed. Rep. of Germany

[21] Appl. No.: 74,406

[22] Filed: Sep. 10, 1979

[30] Foreign Application Priority Data

Sep. 20, 1978 [DE] Fed. Rep. of Germany ....... 2840830

[51] Int. Cl.³ .............................................. A61K 7/13
[52] U.S. Cl. .......................................... 8/407; 8/408; 8/409; 8/410; 8/412
[58] Field of Search ................... 8/10.2, 408, 410, 407, 8/409, 412

[56] References Cited

U.S. PATENT DOCUMENTS

| | | | |
|---|---|---|---|
| 3,506,389 | 4/1970 | Chasle et al. ............................ | 8/10.2 |
| 3,977,826 | 8/1976 | Iscourtz ................................. | 8/10.2 |

OTHER PUBLICATIONS

Cram and Hammond, Organic Chem., pp. 664–665, (1964).
Merck Index, Ninth Edition, (1976), pp. 8879–8890.

*Primary Examiner*—Ethel G. Love
*Attorney, Agent, or Firm*—Michael J. Striker

[57] ABSTRACT

A hair coloring composition, and a method for using the composition, are described, in which as coupler substance, in addition to customary couplers if desired, a compound of the formula

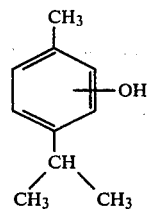

is employed. The novel couplers are more physiologically suitable for use in hair colorings than the prior art couplers, and allow for the preparation of compositions which lead to highly stable colorings over a broad range of shades and tones.

12 Claims, No Drawings

METHOD AND COMPOSITION FOR HAIR COLORING

BACKGROUND OF THE INVENTION

The invention relates to a composition and a method for the oxidative coloring of hair, using a 1-methyl-4-isopropyl-hydroxybenzene as coupler substance.

For the coloring of hair, oxidative coloring compositions have a tremendous significance. The coloring takes place through the reaction of specific developers with specific coupler substances in the presence of a suitable oxidation agent.

As developer substances, 1,4-diaminobenzene, 2,5-diaminotoluene, 3-methyl-4-aminophenol and p-aminophenol have been employed. Among others, resorcinol, 4-chlororesorcinol, α-naphthol, 2,4-diaminotoluene, 2,4-diaminoanisole, 2,4-diaminophenoxyethanol, 2,5-dimethylphenol and m-aminophenol are used as coupler substances.

There are numerous requirements which must be met by oxidation coloring agents which are to be used for the coloring of human hair. They must be toxicologically and dermatologically suitable for such use; moreover, they must permit the achievement of coloring of the desired intensity. It is also necessary that through the combination of suitable developer and coupler components a broad palette of various color nuances might be achieved. Further, good tolerances to light, permanent wave treatments, acid and rubbing are required. In any event, the hair colorings should remain stable over a period of at least 4 to 6 weeks without negative influence from light, rubbing and chemical agents.

This large number of requirements cannot be fully satisfactorily met through the use of the known oxidation hair coloring agents. This holds true both for the phenolic coupler substances α-naphthol and 2,5-dimethylphenol and for m-phenylenediamine and derivatives 2,4-diaminoanisole, 2,4-diaminotoluene and 2,4-diaminophenoxyethanol.

On account of their physiological hazard, some of the named coupler substances, namely 2,5-dimethylphenol, 2,4-diaminoanisole and 2,4-diaminotoluene, have limited practical significance. In addition, the range in which they still are employed is ever narrower. Another physiologically deleterious coupler substance is the above-mentioned 2,4-diaminophenoxyethanol.

In addition to the noted physiological and dermatological considerations, the blue- and violet-tones which can be achieved with the coupler substances mentioned have not been truly satisfactory with respect to their being fast to wear. This is true for the blue obtained by the oxidative route through the combination of developer 1,4-diaminobenzene or 2,5-diaminotoluene with the coupler substance m-phenylenediamine: even without external influences, the color rapidly turns to red. With the use of 2,4-diaminotoluene as coupler the fast to wear properties of the coloring achieved are similarly unsatisfactory.

Much less light tolerant are the violet shades obtained with the developer/coupler combination 2,5-diaminotoluene or 1,4-diaminobenzene and α-naphthol.

DESCRIPTION OF THE INVENTION

It is therefore an object of the invention to provide agents for the oxidative coloring of hair based on coupler substances, which possess better physiological properties than the corresponding couplers of the prior art, and which in combination with the known developer substances, such as 1,4-diaminobenzene, 2,5-diaminotoluene and p-aminophenol, lead to coloring with good wear properties and sufficient intensity.

It is also an object of the invention to provide a method for using the novel compositions for the coloring of human hair.

It has been found that these objects can be achieved through the use of a 1-methyl-4-isopropyl-hydroxybenzene of the general formula

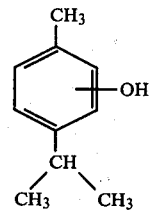

as coupler substance in oxidative coloring of hair.

The compounds used as coupler substances in the inventive hair coloring compositions, namely 1-methyl-4-isopropyl-2-hydroxybenzene and 1-methyl-4-isopropyl-3-hydroxybenzene, are well soluble in mixtures of water and alcohol. The solubility can also be increased through the addition of alkali, such as sodium hydroxide. The novel couplers, in particular as components of the novel hair coloring compositions, also exhibit excellent storage stability.

As examples of developer substances which can be used in the hair coloring compositions of the invention may be mentioned p-aminophenol, 3-methyl-4-aminophenol, 1,4-diaminobenzene, 2,5-diaminotoluene and 2,5-diaminobenzyl alcohol.

In the hair coloring compositions, the coupler substances of the above-noted general formula should be present in a concentration of between about 0.01 to 3.0 weight-%, and preferably between 0.1 to 3.0 weight-%. Of the couplers, 1-methyl-4-isopropyl-3-hydroxybenzene, commonly known under the trivial name thymol, is preferred.

The hair coloring compositions of the present application may also contain additional known coupler substances, for example, resorcinol, 4-chlororesorcinol, m-aminophenol, 3,4-diaminobenzoic acid and 6-methyl-3-aminophenol.

The coupler component is added in general in approximately an equimolar amount with reference to the developer. It is nonetheless not disadvantageous, if the coupler component or the developer were to be present in excess.

It is further not necessary that the developer/coupler combination consist of only a single developer or coupler: in many cases, it may include a number of developers and couplers.

The total amount of oxidation coloring agents in the inventive compositions, consisting of the developer and the coupler, should advantageously be between about 0.1 and 5.0 weight-%, preferably 0.5 to 3.0 weight-%.

In addition, it is possible to add known directly-applicable coloring agents to the compositions, such as triphenylmethane dyes like Diamond Fuchsin (C.I. 42 510) and Leather Ruby HF (C.I. 42 520), aromatic nitro dyes such as 2-nitro-1,4-diaminobenzene, azo dyes like Acid Brown 4 (C.I. 14 805), anthraquinone dyes like Disperse Red 15 (C.I. 60 710), or 1,4,5,8-tetraaminoanthraquinone and 1,4-diaminoanthraquinone.

Further cosmetic additives, such as antioxidants like ascorbic acid or sodium sulfite, alkali hydroxides, complex-forming agents, perfume oils, wetting agents, emulsifiers, thickeners, and hair care agents may be present in the compositions.

The application form may be a solution, preferably a gel, a creme or an emulsion. The preparation involves a mixing of the coloring components with the customary components of the particular application form. Such customary components in cremes, emulsions or gels include wetting agents or emulsifiers from the class of anionic or nonionic surface active substances such as fatty alcohol sulfates, fatty acid alkanolamides, alkyl sulfonates, alkyl benzene sulfonates, oxethylated fatty alcohols, oxethylated nonyl phenols, as well as thickeners such as higher fatty alcohols, fats, cellulose derivatives, paraffin oil and fatty acids, or other hair care agents such as lanolin derivatives, cholesterin and pantothenic acid. These additives are used in amounts customary for such compositions; for example, the wetting agents and emulsifiers are present in concentrations between about 0.5 to 30 weight-%, while thickeners may comprise between about 0.1 to 25 weight-% of the composition.

Depending upon the particular components, the coloring compositions of the invention may react under slightly acidic, neutral or alkaline conditions. In particular, they often have a pH value in the alkaline range between 8.0 and 11.5, in which case the preparation usually takes place with ammonia. Nevertheless, other known organic amines, such as monoethanolamine or triethanolamine, can also find application.

According to the inventive process for oxidative coloring of hair, one mixes the coloring composition, consisting of a combination of customary developer with a 1-methyl-4-isopropyl-hydroxybenzene of the above general formula as coupler, if desired with additional known couplers, with an oxidation agent shortly prior to use, and then applies the mixture to the hair. As oxidation agent for development of the hair color, hydrogen peroxide, for example as 6% aqueous solution, or its addition products with urea, melamine or sodium borate, can be used. One allows the mixture to work on the hair at between about 15° and 50° C. for about 10 to 45 minutes, after which the hair is rinsed with water and dried. If desired, after the rinsing the hair may be washed with shampoo and rinsed with a weak organic acid, such as citric or tartaric acid.

The compositions thus obtained using 1-methyl-4-isopropyl-hydroxy-benzenes as coupler lead to hair colorings with excellent fast to wear properties, in particular light, washing and rubbing stability, and can be removed through the use of reducing agents.

With respect to color possibilities, the novel compositions provide a broad pallette of various colors, depending upon type and composition, which range over blond to brown, purple, violet all the way to blue and black tones.

So for example with the coupler/developer combination 1-methyl-4-isopropyl-3-hydroxybenzene/ 2,5-diaminotoluene, an oxidative blue coloration with the desired stability can be obtained. A more violet tone which is even more intensely blue can be achieved with 1-methyl-4-isopropyl-3-hydroxybenzene and 1,4-diaminobenzene as developer. These colorings are noteworthy in their stability to permanent wave treatments.

Of particular significance is the fact that 1-methyl-4-isopropyl-3-hydroxybenzene can be used as coupler not only with 1,4-diamines, but also with p-aminophenol hair colorings to advantage. Thus, the combination of developer p-aminophenol with 1-methyl-4-isopropyl-3-hydroxybenzene leads to a suitable red coloring under oxidative conditions.

Particularly interesting is the fact that the coupler substance 1-methyl-4-isopropyl-3-hydroxybenzene can be used as nuancer when other couplers are present in excess.

In addition to the advances achieved with respect to the dermatological and toxicological properties through the use of the physiologically well-compatible 1-methyl-4-isopropyl-hydroxybenzenes, their fungicidal and bactericidal effectiveness are also of significance. Thus, for example, the antiseptic effectiveness of 1-methyl-4-isopropyl-3-hydroxybenzene is twenty times higher than that of phenol. Through this property, the 1-methyl-4-isopropyl-3-hydroxybenzene serves not only as coloring agent but also as preservative.

A further advantage of 1-methyl-4-isopropyl-3-hydroxybenzene for its use in the inventive hair coloring compositions lies in its ethereal odor. This odor overcomes that of the ammonia added as alkalizing agent and minimizes the need for additional perfuming.

The invention may be better understood through the following examples.

EXAMPLE 1

Hair coloring solution

| | |
|---|---|
| 2.0 g | 1-methyl-4-isopropyl-3-hydroxybenzene |
| 1.6 g | p-aminophenol |
| 0.6 g | sodium hydroxide, solid |
| 0.4 g | sodium sulfite, anhydrous |
| 10.0 g | lauryl alcohol-diglycol ether sulfate, sodium salt (28% aqueous solution) |
| 10.0 g | isopropanol |
| 10.0 g | ammonia, 23% |
| 65.4 g | water |
| 100.0 g | |

Shortly before application 50 g of this hair coloring composition is mixed with 50 ml hydrogen peroxide solution (6%). The mixture is allowed to react for 30 minutes at 40° C. in blond human hair. Thereafter, the hair is rinsed with water and dried. The hair has a luminous red coloration.

EXAMPLE 2

Hair coloring composition in gel form

| | |
|---|---|
| 0.6 g | 1-methyl-4-isopropyl-3-hydroxybenzene |
| 0.4 g | 1,4-diaminobenzene |
| 0.2 g | sodium hydroxide, solid |
| 0.4 g | sodium sulfite, anhydrous |
| 15.0 g | oleic acid |
| 7.0 g | isopropanol |
| 10.0 g | ammonia, 23% |
| 66.4 g | water, completely salt-free |
| 100.0 g | |

50 g of the above hair coloring mixture is mixed shortly before application with 50 ml 6% hydrogen peroxide solution; the mixture is then applied to blond human hair. After a period of 30 minutes at 40° C. the hair is rinsed with water and dried. The hair is colored in an intense violet-tinted blue tone.

EXAMPLE 3

Hair coloring composition in creme form

| | |
|---|---|
| 0.40 g | 1-methyl-4-isopropyl-3-hydroxybenzene |
| 0.50 g | 2,5-diaminotoluene, with 1 Mol H$_2$SO$_4$ per Mol diamine |
| 0.13 g | sodium hydroxide, solid |
| 0.30 g | sodium sulfite, anhydrous |
| 3.50 g | lauryl alcohol-diglycol ether sulfate, sodium salt (28% aqueous solution) |
| 15.00 g | cetyl alcohol |
| 10.00 g | ammonia, 23% |
| 70.17 g | water |
| 100.00 g | |

Shortly before use 50 g of this hair coloring composition is mixed with 50 ml hydrogen peroxide solution (6%) and allowed to remain in blond human hair for 30 minutes at 40° C. The hair is then rinsed with water and dried. The hair has a color-fast, clear blue coloring.

All of the above percentages are in terms of weight percent.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A composition for oxidative coloring of hair, comprising an oxidizable developer-coupler combination comprising a 1-methyl-4-isopropyl-hydroxybenzene of the formula

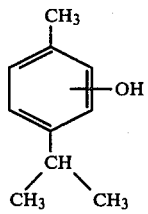

as coupler substance and a developer therefor.

2. A composition as defined in claim 1, wherein said coupler substance is 1-methyl-4-isopropyl-3-hydroxybenzene.

3. A composition as defined in claim 1, wherein said coupler substance is present in a concentration between 0.01 and 3.0 weight-%.

4. A composition as defined in claim 1, wherein said coupler substance is present in a concentration between 0.1 and 3.0 weight-%.

5. A composition as defined in claim 1, wherein said developer includes at least one of 2,5-diaminotoluene, 1,4-diaminobenzene and p-aminophenol.

6. A composition as defined in claim 1, wherein the developer-coupler combination comprises 0.1 to 5.0 weight-% of the composition.

7. A composition as defined in claim 1, wherein the developer-coupler combination comprises between 0.5 to 3.0 weight-% of the composition.

8. A composition as defined in claim 1, wherein at least one directly-applicable coloring agent selected from the group consisting of Diamond Fuchsin, Leather Ruby HF, 2-nitro-1,4-diaminobenzene, Acid Brown 4, Disperse Red 15, 1,4,5,8-tetraaminoanthraquinone and 1,4-diamino-anthraquinone is added.

9. A composition as defined in claim 1, wherein at least one antioxidant, preferably ascorbic acid or sodium sulfite, is added.

10. A composition as defined in claim 1, wherein at least one additional coupler substance selected from the group consisting of resorcinol, 4-chlororesorcinol, m-aminophenol, 3,4-diaminobenzoic acid and 6-methyl-3-aminophenol is added.

11. A composition as defined in claim 1, further comprising wetting agents and/or emulsifiers selected from the class of anionic or nonionic surface active substances and/or thickeners selected from higher fatty alcohols, fats, cellulose derivatives, paraffin oil and fatty acids.

12. A process for oxidative coloring of hair, comprising forming an oxidizable developer-coupler combination of a developer substance with a 1-methyl-4-isopropylhydroxybenzene of the formula

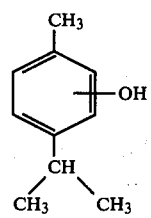

as coupler substance, and with an oxidation agent, preferably hydrogen peroxide;
applying said combination to hair;
rinsing the hair after between about 10 to 45 minutes at a temperature between 15° to 50° C.; and
drying the hair.

* * * * *